US012369962B2

(12) United States Patent
Coulombe et al.

(10) Patent No.: US 12,369,962 B2
(45) Date of Patent: Jul. 29, 2025

(54) METHOD AND APPARATUS FOR DETERMINING BRONCHIAL DENERVATION

(71) Applicant: Medtronic CryoCath LP., Toronto (CA)

(72) Inventors: Nicolas Coulombe, Anjou (CA); Zhongping Yang, Woodbury, MN (US); Jean-Pierre Lalonde, Candiac (CA)

(73) Assignee: Medtronic CryoCath LP., Toronto (CA)

( * ) Notice: Subject to any disclaimer, the term of this patent is extended or adjusted under 35 U.S.C. 154(b) by 724 days.

(21) Appl. No.: 17/674,108

(22) Filed: Feb. 17, 2022

(65) Prior Publication Data

US 2022/0257299 A1     Aug. 18, 2022

Related U.S. Application Data (60) Provisional application No. 63/150,330, filed on Feb. 17, 2021.

(51) Int. Cl.
| | |
|---|---|
| *A61B 18/14* | (2006.01) |
| *A61B 18/02* | (2006.01) |
| *A61B 18/00* | (2006.01) |

(52) U.S. Cl.
CPC .......... *A61B 18/02* (2013.01); *A61B 18/1492* (2013.01); *A61B 2018/0025* (2013.01);
(Continued)

(58) Field of Classification Search
CPC ................ A61B 18/02; A61B 18/1492; A61B 2018/0025; A61B 2018/00541;
(Continued)

(56) References Cited

U.S. PATENT DOCUMENTS

| | | |
|---|---|---|
| 7,412,977 B2 | 8/2008 | Fields et al. |
| 7,938,123 B2 | 5/2011 | Danek et al. |
| | (Continued) | |

FOREIGN PATENT DOCUMENTS

| | | |
|---|---|---|
| EP | 3120792 A1 | 1/2017 |
| EP | 3244820 B1 | 6/2020 |
| | (Continued) | |

OTHER PUBLICATIONS

International Search Report dated May 16, 2019, for International Application No. PCT/CA2019/050226 filed on Feb. 26, 2019; Consisting of 8 pages.

(Continued)

*Primary Examiner* — Ankit D Tejani
*Assistant Examiner* — Joshua Brendon Solomon
(74) *Attorney, Agent, or Firm* — Michael Best & Friedrich LLP (57) ABSTRACT

A method of performing bronchial denervation of a bronchus having bronchial nerves along a portion thereof is provided. The method includes providing a cryoablation device having multiple electrodes capable of delivering electrical energy and measuring impedance. At least one bronchial nerve is stimulated with electrical energy. The electrical signals from the at least one bronchial nerve are recorded to provide a first value representative of nerve function. Cryogenic treatment energy is applied to form ice in the bronchus having a thickness to encapsulate the at least one bronchial nerve to cause a reduction in nerve function. The at least one bronchial nerve is restimulated with electrical energy. The electrical signals are recorded from the restimulated at least one bronchial nerve to provide a second value that represents diminished nerve function. The first value and the second value are compared to provide an assessment of the reduction in nerve function.

20 Claims, 7 Drawing Sheets

(52) U.S. Cl.
CPC .............. *A61B 2018/00541* (2013.01); *A61B 2018/00577* (2013.01); *A61B 2018/00875* (2013.01); *A61B 2018/0212* (2013.01); *A61B 2018/1467* (2013.01)

(58) Field of Classification Search
CPC ........... A61B 2018/00577; A61B 2018/00875; A61B 2018/0212; A61B 2018/1467; A61B 2018/0022; A61B 2018/00255
See application file for complete search history.

(56) References Cited

U.S. PATENT DOCUMENTS

| | | |
|---|---|---|
| 8,088,127 B2 | 1/2012 | Mayse et al. |
| 9,095,321 B2 | 8/2015 | Phelan et al. |
| 9,144,449 B2 | 9/2015 | Burr et al. |
| 9,198,707 B2 | 12/2015 | McKay et al. |
| 10,328,281 B2 | 6/2019 | Stopek |
| 10,524,859 B2 | 1/2020 | Vrba et al. |
| 2007/0255162 A1 | 11/2007 | Abboud et al. |
| 2008/0312644 A1 | 12/2008 | Fourkas et al. |
| 2009/0192505 A1 | 7/2009 | Askew et al. |
| 2009/0205665 A1 | 8/2009 | Tanaka et al. |
| 2009/0299355 A1 | 12/2009 | Bencini et al. |
| 2010/0249765 A1 | 9/2010 | Johnston |
| 2011/0152855 A1 | 6/2011 | Mayse et al. |
| 2012/0136418 A1 | 5/2012 | Buckley et al. |
| 2012/0191081 A1 | 7/2012 | Markowitz |
| 2012/0310226 A1 | 12/2012 | Fourkas et al. |
| 2014/0257271 A1* | 9/2014 | Mayse ............... A61B 18/1492 606/41 |
| 2014/0358140 A1* | 12/2014 | Emmons ............ A61B 18/1815 606/33 |
| 2015/0141813 A1 | 5/2015 | Weadock |
| 2015/0157382 A1 | 6/2015 | Avitall et al. |
| 2015/0173673 A1 | 6/2015 | Toth et al. |
| 2015/0265334 A1 | 9/2015 | Franke et al. |
| 2015/0272666 A1 | 10/2015 | Wang |
| 2017/0189106 A1 | 7/2017 | Schuler et al. |
| 2017/0319853 A1 | 11/2017 | Yamasaki et al. |
| 2018/0199976 A1 | 7/2018 | Fischer |
| 2018/0310978 A1* | 11/2018 | Avitall .................. A61B 5/6853 |
| 2019/0026056 A1 | 1/2019 | Wang et al. |
| 2019/0262056 A1 | 8/2019 | Yang et al. |
| 2019/0365452 A1 | 12/2019 | Avitall et al. |
| 2020/0000514 A1 | 1/2020 | Weadock |
| 2020/0060758 A1 | 2/2020 | Rajagopalan et al. |
| 2020/0129220 A1 | 4/2020 | Jung |
| 2021/0128232 A1* | 5/2021 | Jung ..................... A61B 5/367 |

FOREIGN PATENT DOCUMENTS

| | | |
|---|---|---|
| WO | 2012019156 A1 | 2/2012 |
| WO | 2012027641 A2 | 3/2012 |
| WO | 2015120325 A1 | 8/2015 |
| WO | 2016033017 A1 | 3/2016 |
| WO | 2016109437 A1 | 7/2016 |
| WO | 2017214183 A1 | 12/2017 |

OTHER PUBLICATIONS

European Patent Office, Supplementary European Search Report, dated Nov. 2, 2021, for corresponding European Application No. EP 19761431; consisting of 7 pages.

Yan-Lin Yang, et al., Optimal Esophageal Balloon Volume for Accurate Estimation of Pleural Pressure at End-Expiration and End-Inspiration: an in Vitro Bench Experiment, Intensive Care Medicine Experimental, Aug. 2, 2017 (Aug. 2, 2017), DOI: 10.1186/s40635-017-0148-z, 12 pages.

International Search Report and Written Opinion dated Nov. 4, 2021, for corresponding International Application No. PCT/US2021/043178; International Filing Date: Jul. 26, 2021, consisting of 17-pages.

International Search Report and Written Opinion for Application No. PCT/CA2022/050231 dated Nov. 15, 2022 (15 pages).

European Patent Office Extended Search Report for Application No. 22794126.7 dated Dec. 10, 2024 (7 pages).

* cited by examiner

METHOD AND APPARATUS FOR DETERMINING BRONCHIAL DENERVATION

CROSS-REFERENCE TO RELATED APPLICATION

This application claims the benefit of U.S. Provisional Application Ser. No. 63/150,330.

FIELD

The present technology is generally related to bronchial denervation, and in particular, methods and apparatus for and performing bronchial denervation.

BACKGROUND

Air passages within the lungs known as bronchial tubes or bronchi include a network of nerves that surround the bronchi and are at least partially responsible for constriction and dilation of the bronchi. It has been suggested that selective treatment of bronchial nerves to affect their functionality, such as by diminishing it, could help compromised patients breathe better. It has also been suggested that selective bronchial denervation (impairment or cessation of nerve function) could alleviate pain and discomfort for patients suffering from non-curable illnesses such as Chronic Obstructive Pulmonary Disease (COPD).

Ablation technologies, such as radio frequency and cryotherapy, are known for ablating tissue and could be used to affect nerves to create either long-term but reversible impairment or permanent nerve impairment. However, it is difficult to monitor ablation in bronchial tissue using current imaging technologies (ultrasounds, MRI, CT) as they have difficulty imaging tissue surrounded by air, such as in lungs.

SUMMARY

The techniques of this disclosure generally relate to methods and apparatus for performing bronchial denervation.

A method of performing bronchial denervation of a bronchus having bronchial nerves along a portion thereof is provided. The method includes providing a cryoablation device having multiple electrodes capable of delivering electrical energy and measuring impedance. At least one bronchial nerve is stimulated with electrical energy from at least a portion of the multiple electrodes of the cryoablation device. The electrical signals from the at least one bronchial nerve are recorded to provide a first value representative of nerve function. Cryogenic treatment energy is applied using the cryoablation device to form ice having a thickness to encapsulate at least one bronchial nerve to cause a reduction in nerve function. The at least one bronchial nerve is restimulated with electrical energy from at least a portion of the multiple electrodes of the cryoablation device. The electrical signals are recorded from the restimulated at least one bronchial nerve to provide a second value that represents diminished nerve function. The first value and the second value are compared to provide an assessment of the reduction in nerve function.

When comparing the first and second values if the second value is more than 50% of the first value, part of the method is repeated. Cryogenic treatment energy is applied again to the at least one bronchial nerve using the cryoablation device to form ice having a thickness to encapsulate at least one bronchial nerve to cause a reduction in nerve function in the at least one bronchial nerve. The at least one bronchial nerve is restimulated with electrical energy from at least a portion of the multiple electrodes of the cryoablation device. Electrical signals are again recorded from the restimulated at least one bronchial nerve to provide a third value that represents diminished nerve function. The first value and the third value are then compared to provide an updated assessment of the nerve function.

The cryoablation device can include a balloon catheter having multiple electrodes disposed on an exterior surface of the balloon. Additionally, the cryoablation device can include an elongate flexible shaft extending from a distal end of the balloon, and wherein the elongate flexible shaft includes at least a portion of the multiple electrodes.

The method can further include placing the cryoablation device within a bronchus prior to stimulating the at least one bronchial nerve.

The method can further include measuring an impedance using at least a portion of the multiple electrodes proximate the bronchial nerve and correlating the measured impedance to ice thickness.

The cryoablation device can further include a mapping catheter that extends distally from the balloon catheter. The mapping catheter can be used to record electrical signals distal of the balloon catheter to further confirm the reduction of nerve functionality.

The cryoablation device can form ice having a thickness of at least 3 mm to encapsulate at least one bronchial nerve to cause a reduction in nerve function.

The electrical energy used to stimulate the at least one bronchial nerve can be non-ablative energy. However, the reduction of nerve functionality can be permanent if desired.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Before describing in detail exemplary embodiments, it is noted that the embodiments reside primarily in combinations of apparatus components and processing steps related to feedback control systems for cryo-mapping and cryoablation. Accordingly, components have been represented where appropriate by conventional symbols in the drawings, showing only those specific details that are pertinent to understanding the embodiments so as not to obscure the disclosure with details that will be readily apparent to those of ordinary skill in the art having the benefit of the description herein. Like numbers refer to like elements throughout the description.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
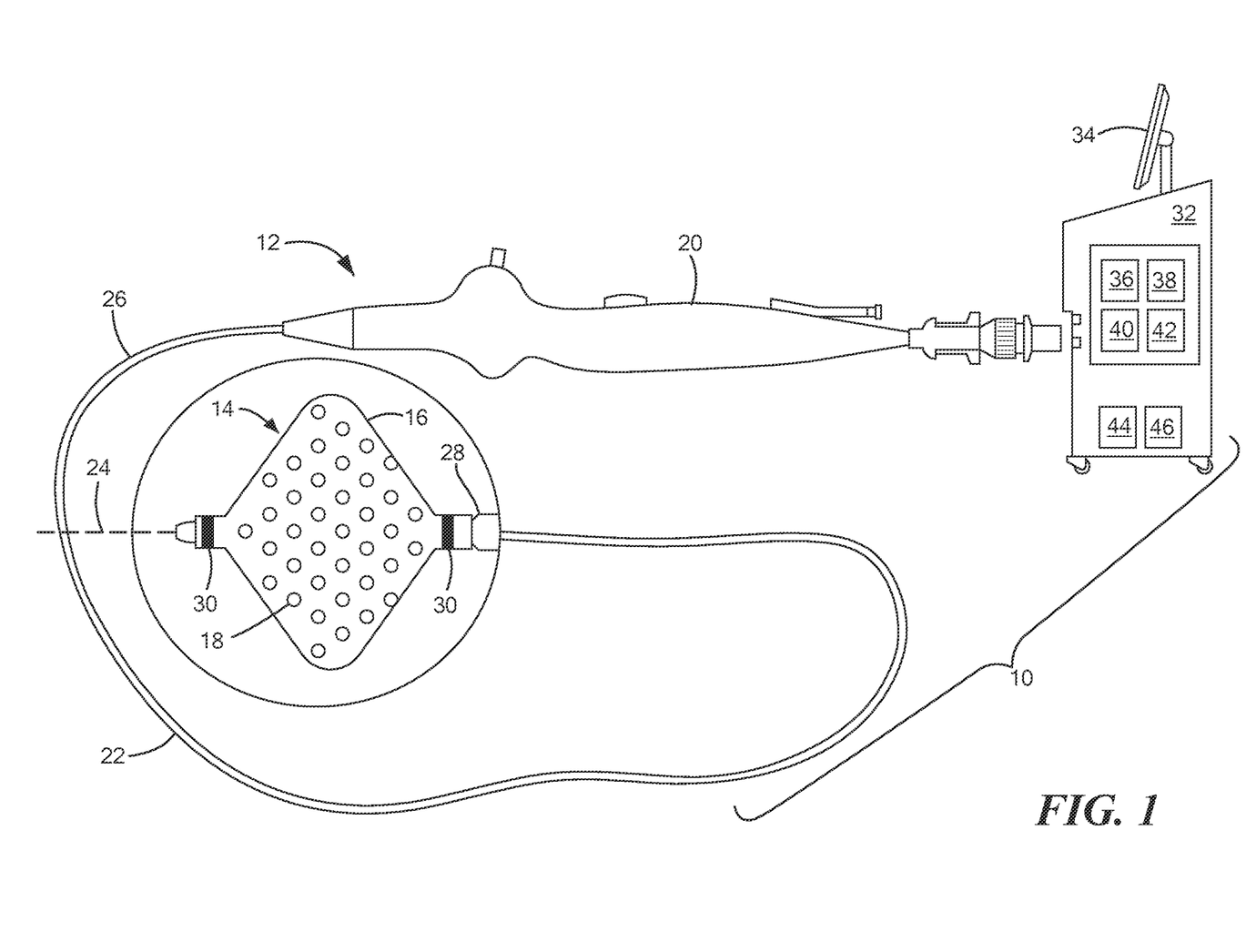
FIG. 1 shows an exemplary system for bronchial denervation, the system including a cryoablation device.

Referring now to FIG. 1, an exemplary medical system 10 for bronchial denervation is shown. As used herein, denervation refers to temporary or permanent impairment of nerve function, such as the ability of the nerve to conduct signals along its length. Complete impairment or cessation of nerve function at a specific location is referred to as a conduction block. The block can be temporary if the nerves recover function or permanent if they do not.

In one embodiment, the medical system 10 generally includes a treatment device, such as a cryoablation device 12, having one or more treatment elements 14, and a control unit 32 in communication with the cryoablation device 12. Although the cryoablation device 12 is described herein as operating to reduce the temperature of target tissue to denervate nerves within the lungs, it will be understood that the cryoablation device 12 also may be used with one or more additional modalities, such as radiofrequency (RF) ablation, pulsed field ablation, ultrasound ablation, microwave ablation, or the like.

The one or more treatment elements 14 are configured to deliver cryogenic therapy, and may further be configured to deliver radiofrequency energy, pulsed field ablation energy, or the like for energetic transfer with the area of targeted tissue, such as pulmonary tissue. In particular, the treatment element(s) 14 are configured to reduce the temperature of adjacent tissue in order to perform cryogenic treatment resulting in denervation.

For example, the treatment elements(s) 14 may include one or more balloons 16 (as shown in FIG. 1), which may be compliant or non-compliant, within which a coolant, such as liquid nitrogen, argon, supercritical fluid, or nitrogen dioxide may be circulated in order to reduce the temperature of the balloon 16 down to temperatures between −20°-75° C. Additionally, the treatment element(s) 14 may include other thermally and/or electrically-conductive components, such as one or more electrodes 18 in communication with the control unit 32. In one configuration, the electrodes 18 are disposed around a circumference of the balloon 16, either over much of an outer surface of the balloon 16 or a portion thereof. In another configuration, the electrodes 18 include electrodes 30 that are disposed immediately proximate and distal to the balloon 16.

In one or more embodiments, the processing circuitry 36 may include a processor 40 and a memory 42 in addition to or instead of a processor 40, such as a central processing unit, and memory, the processing circuitry 36 may comprise integrated circuitry for processing and/or control, e.g., one or more processors and/or processor cores and/or FPGAs (Field Programmable Gate Array) and/or ASICs (Application Specific Integrated Circuitry) adapted to execute instructions. The processor 40 may be configured to access (e.g., write to and/or read from) the memory 42, which may comprise any kind of volatile and/or nonvolatile memory, e.g., cache and/or buffer memory and/or RAM (Random Access Memory) and/or ROM (Read-Only Memory) and/or optical memory and/or EPROM (Erasable Programmable Read-Only Memory).

The processing circuitry 36 may be configured to control any of the methods and/or processes described herein and/or to cause such methods, and/or processes to be performed, e.g., by the remote controller 38. Processor 40 corresponds to one or more processors 40 for performing functions described herein. The memory 42 is configured to store data, programmatic software code and/or other information described herein. In some embodiments, the software may include instructions that, when executed by the processor 40 and/or processing circuitry 36 causes the processor 40 and/or processing circuitry 36 to perform the processes described herein with respect to remote controller 38. For example, processing circuitry 36 of the remote controller 38 may include a control unit 32 that is configured to perform one or more functions described herein.

Figure 2:
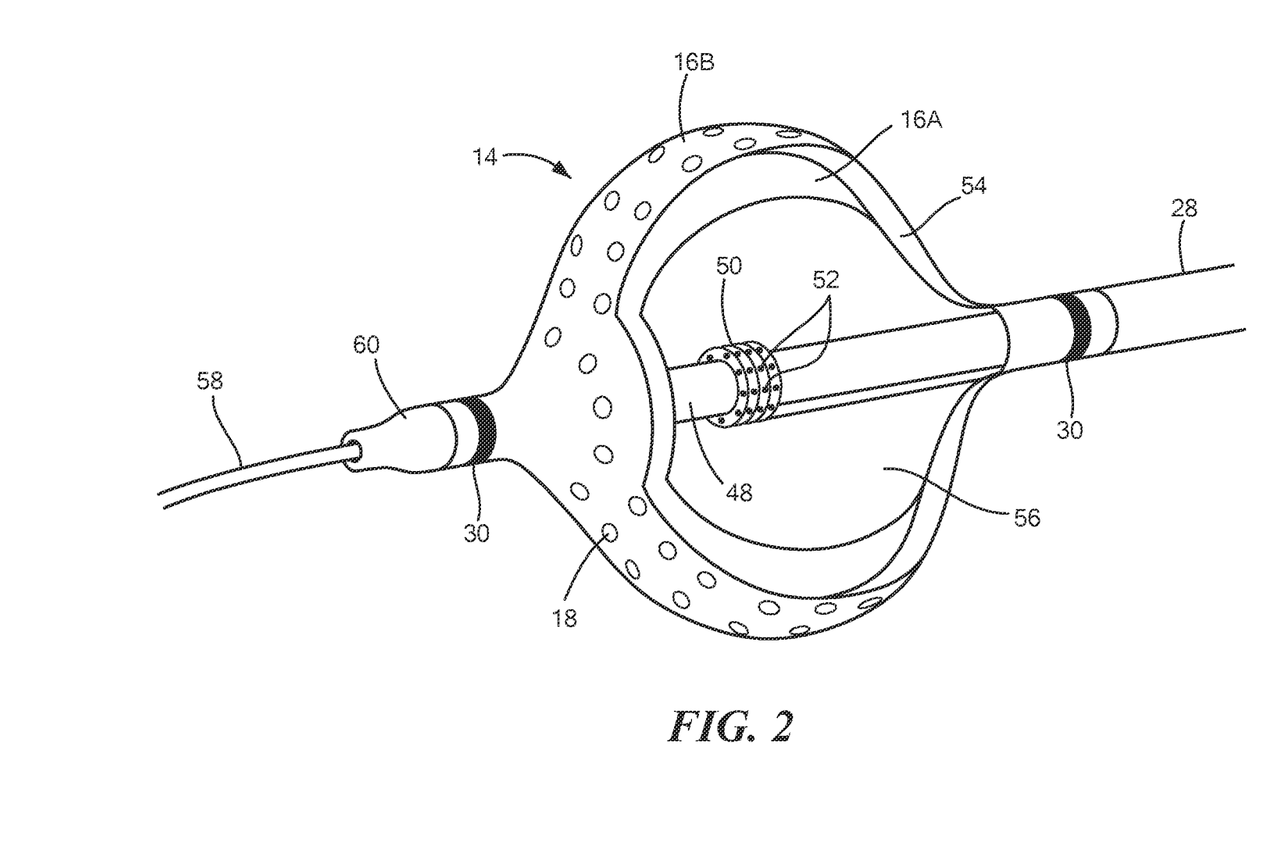
FIG. 2 shows a partial cross-sectional view of the cryoablation device of FIG. 1.

In the embodiment shown in FIG. 1, with a detail view of the cryoablation device 12 shown in FIG. 2, the cryoablation device 12 includes a handle 20 and an elongate body 22 coupled to the handle 20. The elongate body 22 is sized and configured to be passable through a patient's bronchus and/or positionable proximate to a tissue region for diagnosis or treatment. The elongate body 22 defines a longitudinal axis 24, a proximal portion 26, and a distal portion 28, and may further include one or more lumens disposed within the elongate body 22 that provide mechanical, electrical, and/or fluid communication between the proximal portion 26 of the elongate body 22 and the distal portion 28 of the elongate body 22. Further, the treatment element(s) 14 (such as the balloon(s) 16 shown in FIGS. 1 and 2) are coupled to the elongate body distal portion 28. The cryoablation device 12 may additionally include electrodes 30 immediately adjacent proximal and distal to balloon 16. Electrodes 30 may be configured as mapping/reference/navigation electrodes. The electrodes 30 are in electrical communication with the control unit 32. In one embodiment, the cryoablation device 12 further includes a shaft 48 that is longitudinally movable within a lumen of the elongate body 22, such that the shaft 48 may be advanced or retracted within the elongate body 22, to affect the shape and configuration of the treatment element(s) 14. Thus, the length and diameter of the of balloon 16 may be adjustable or fixed. For example, the cryoablation device 12 may include one treatment element 14, and the shaft 48 may be fully advanced when the treatment element 14 is deflated and in a delivery (or first) configuration wherein the treatment element 14 has a minimum diameter suitable, for example, for retraction of the cryoablation device 12 within a sheath for delivery to and removal from the targeted tissue site. Conversely, when the treatment element 14 is inflated or expanded and in a treatment (or second) configuration, the shaft 48 may be advanced or retracted over a distance that affects the size and configuration of the inflated or expanded treatment element 14. Further, the shaft 48 may include a guidewire lumen through which a sensing device, mapping device, guidewire 58, or other system component may be located and extended from the distal end of the cryoablation device 12 (for example, from the distal portion 60 of the shaft 48). When expanded, the treatment element(s) 14 are sized and configured to fit within a targeted bronchus. For example, the expanded treatment element(s) 14 may have a maximum outer diameter and length of between approximately 5 mm and approximately 40 mm (±2 mm). More specifically, the treatment element(s) 14 utilized in bronchial denervation can have an outer diameter length of 15 mm (±2 mm).

In one embodiment, the treatment element 14 includes two balloons: an inner (or first) balloon 16A and an outer (or second) balloon 16B. In the embodiment shown in FIG. 2, a proximal portion of the treatment element 14 is coupled to the distal portion 28 of the elongate body 22 and a distal portion of the treatment element 14 is coupled to a distal portion 60 of the shaft 32. The cryoablation device 12 also includes one or more nozzles, orifices, or other fluid delivery elements 50 for delivering fluid (for example, coolant) to an interior chamber 56 of the treatment element 14 for equatorial distribution. The fluid delivery elements 50 also include ports 52 disposed on the fluid delivery elements 50. Equatorial distribution refers to coolant being delivered at the largest diameter around an imaginary circle within the treatment element 14. For example, fluid may be delivered to the interior chamber 56 of the inner balloon 16A and/or to the interior chamber of the outer cryoballoon 16B (that is, to the interstitial space 54 between the inner 16A and outer 16B balloons). For simplicity, coolant will be referred to herein as being delivered to the interior chamber 56 of the treatment element 14. During operation, coolant may flow from a coolant supply reservoir 44 through a coolant delivery conduit within the elongate body 22 of the cryoablation device 12 to the distal portion 28, where the coolant may then enter the interior chamber 56 of the treatment element 14, such as through the one or more fluid delivery elements 50, where the coolant expands as it absorbs heat. Expanded coolant may then pass from the interior chamber 56 of the treatment element 14 to a coolant recovery reservoir 46 and/or scavenging system through a coolant recovery conduit.

Figure 3:
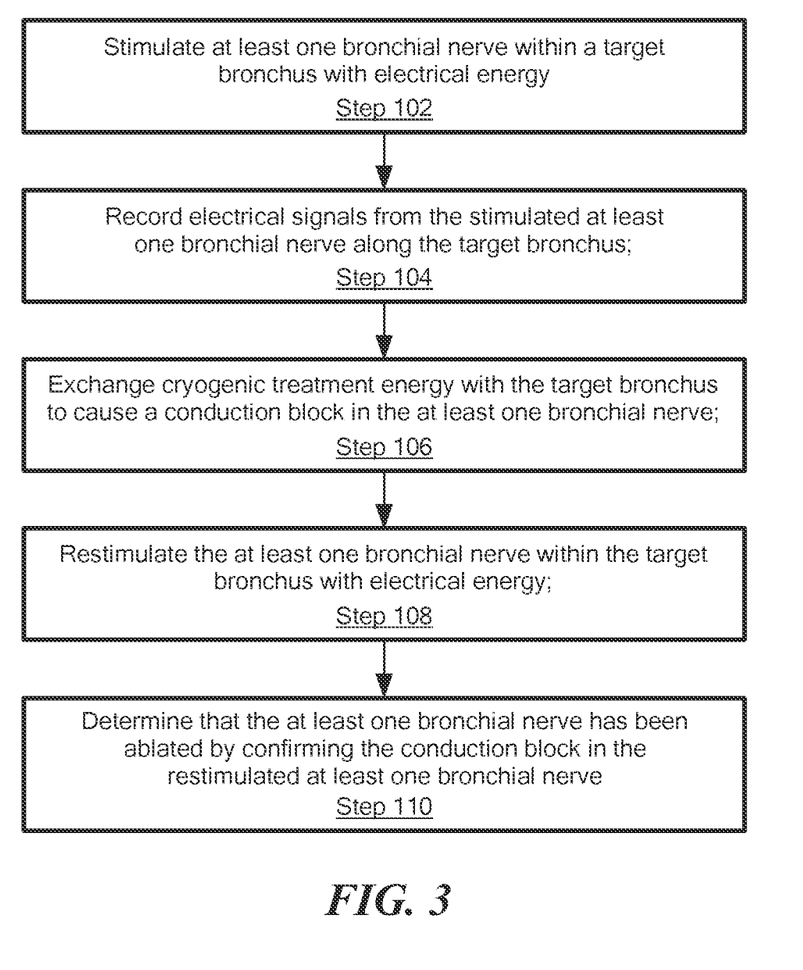
FIG. 3 is a flow chart of an exemplary method of determining bronchial denervation using the system of FIG. 1.

Referring now to FIG. 3, in an exemplary procedure to denervate a target bronchus the shaft 48 having the one or more balloons is advanced to a target position and the balloon 16 is inflated to contact the wall of the bronchus (bronchial wall) 64. In an exemplary configuration, at least a portion of the electrodes 18 on the outer surface of the balloon are utilized to stimulate one or more target bronchial nerves 66 (Step 102). In particular, the electrodes 18 are configured to transfer non-ablative electrical signals 68 such as an electrical pulse to the nerves to propagate an electrical signal along a length of the bronchus to determine the functionality of the nerves in the bronchus. In particular, electrical signals 68 from the stimulated at least one bronchial nerve 66 is recorded along the target bronchus by the (Step 104). In other words, the electrodes 18 may be used to map electrical activity along the bronchus.

Figure 4:
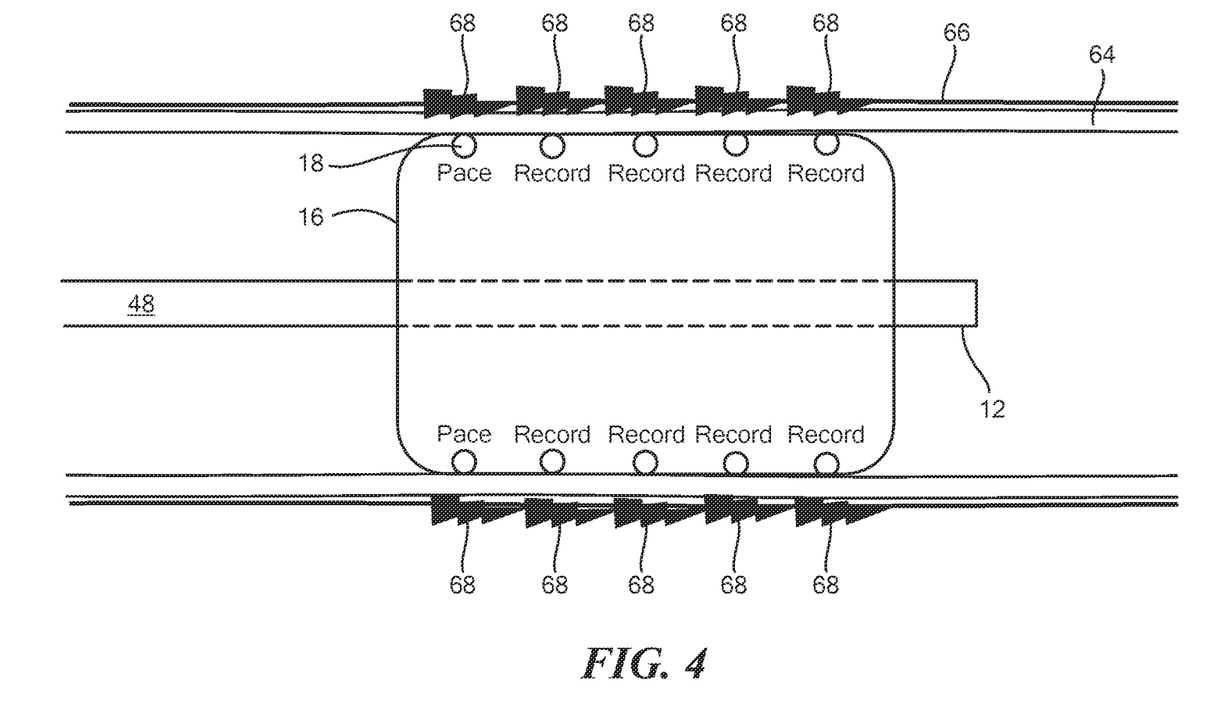
FIG. 4 is a side view inside a target bronchus showing a simplified cryoablation device of FIG. 2 stimulating nerves to innervate the target bronchus in accordance with the method of FIG. 3.

Referring now to FIG. 4, an example of Step 104, electrical signals 68 from the stimulated at least one bronchial nerve 66 is recorded along the target bronchus by at least a portion of the plurality of electrodes 18. In other words, the electrodes 18 may be used to map electrical activity along the bronchus. For example, as shown in FIG. 4, one of the electrodes 18 may be used to pace or otherwise transfer electrical energy to the bronchus while the remaining electrodes 18 record the propagation of that resulting conduction signal wavefront through nerves. The recorded electrical signals 68 are representative of the normal (baseline) nerve function within the target bronchus.

Once the target area of ablation within the bronchus is determined, typically with direct visualization, cryogenic treatment energy is applied to the target bronchus to cause a conduction block 72 in the at least one bronchial nerve which are found circumferentially next to the bronchus (Step 106). For example, cryogenic fluid may be sprayed into the balloon 16 which freezes the target tissue to cause ice formation 76 and a conduction block 72 in the propagated nerve signal. The balloon may be inflated to around 15 mm (±2 mm) within the target bronchus.

In an exemplary treatment, the medical device 12 can bring the balloon 16 to approximately −20° C.-−75° C. at the target bronchial wall 64 for a permanent conduction block 72. The balloon 16 may be slightly oversized to ensure circumferential contact with the bronchial wall 64. The freezing can be performed in multiple freeze-thaw cycles for approximately 2 to 4 minute durations.

At least a portion of the electrodes 18 may be utilized to measure an impedance 70 proximate the bronchial nerve 68. The measured impedance 70 is then correlated to obtain an indirect measure of ice thickness. The ice thickness is then correlated to an extent of freezing or lesion formation 74. Ice thickness is a predictor of lesion depth. Depending on the depth of the bronchial nerve 66 within the bronchial wall 64, the ice formation is an indirect measurement of bronchial nerve 66 denervation success. Typically, the ice thickness may be in the range of at least 3 mm. In an exemplary treatment, the ice thickness can be between 3-4 mm.

Figure 5:
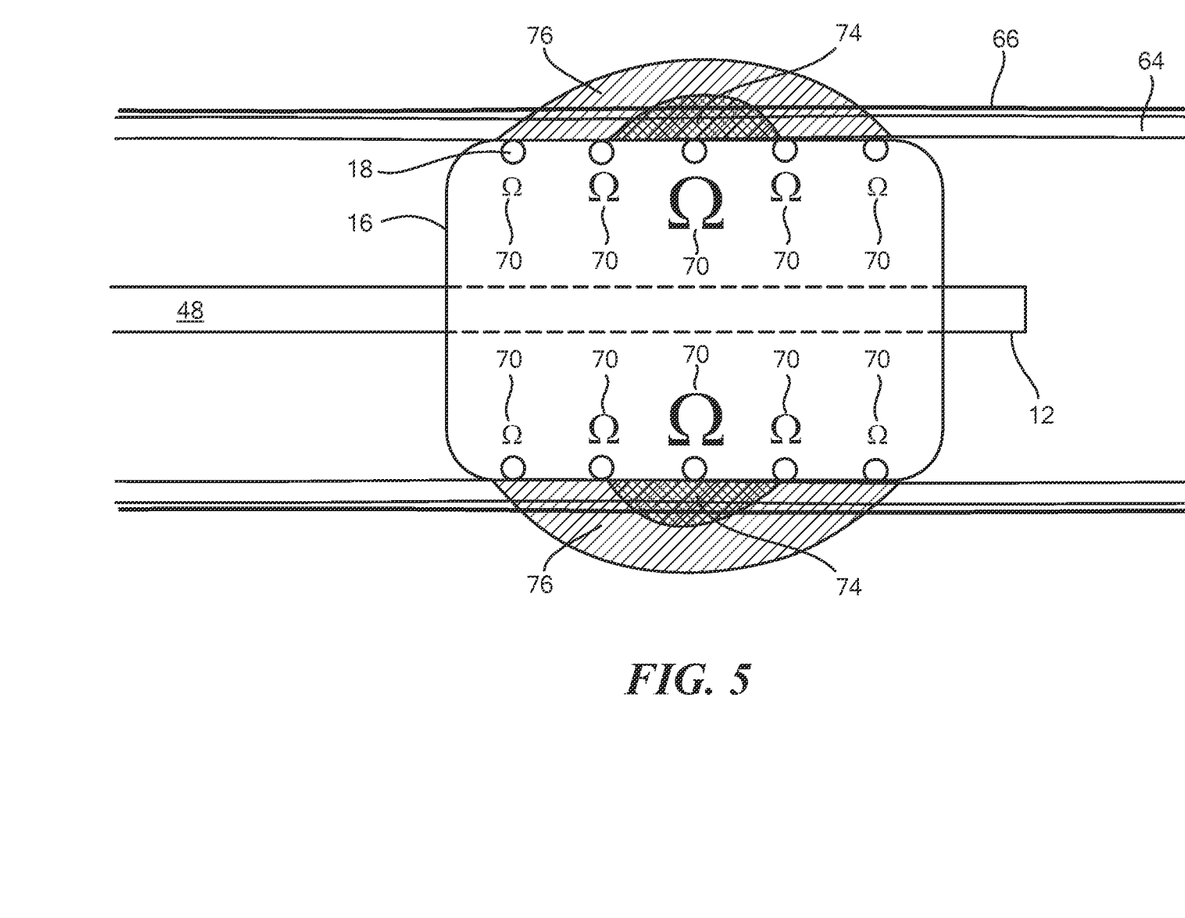
FIG. 5 is a side view of the simplified cryoablation device shown in FIG. 2 showing the impedance being measured during cryoablation of the target bronchus.

Referring now to FIG. 5, an example of Step 106, the electrodes 18 measure an impedance 70 ("Ω") at each electrode 18 during the cryogenic treatment. When the target impedance 70 is reached during the cryogenic treatment of the bronchus, it is determined that the target tissue/nerves has been ablated, whereas surrounding tissue/nerves may have a smaller impedance 70 and not be ablated.

To confirm the ablation, the at least one bronchial nerve 66 is restimulated within the target bronchus with electrical energy via the electrodes 18, and the propagation of the electrical signals 68 are measured (Step 108) via the same electrodes 18. A pacing signal can be sent through the bronchial wall 64 to stimulate the bronchial nerve 66 via the electrodes 18. The resultant excitation is recorded by the electrodes 18. This second recorded electrical signal 68 is representative of diminished nerve function. Typically, if the second recorded electrical signal is less than 50% the first recorded electrical signal 68, then the treatment is considered complete.

Figure 6:
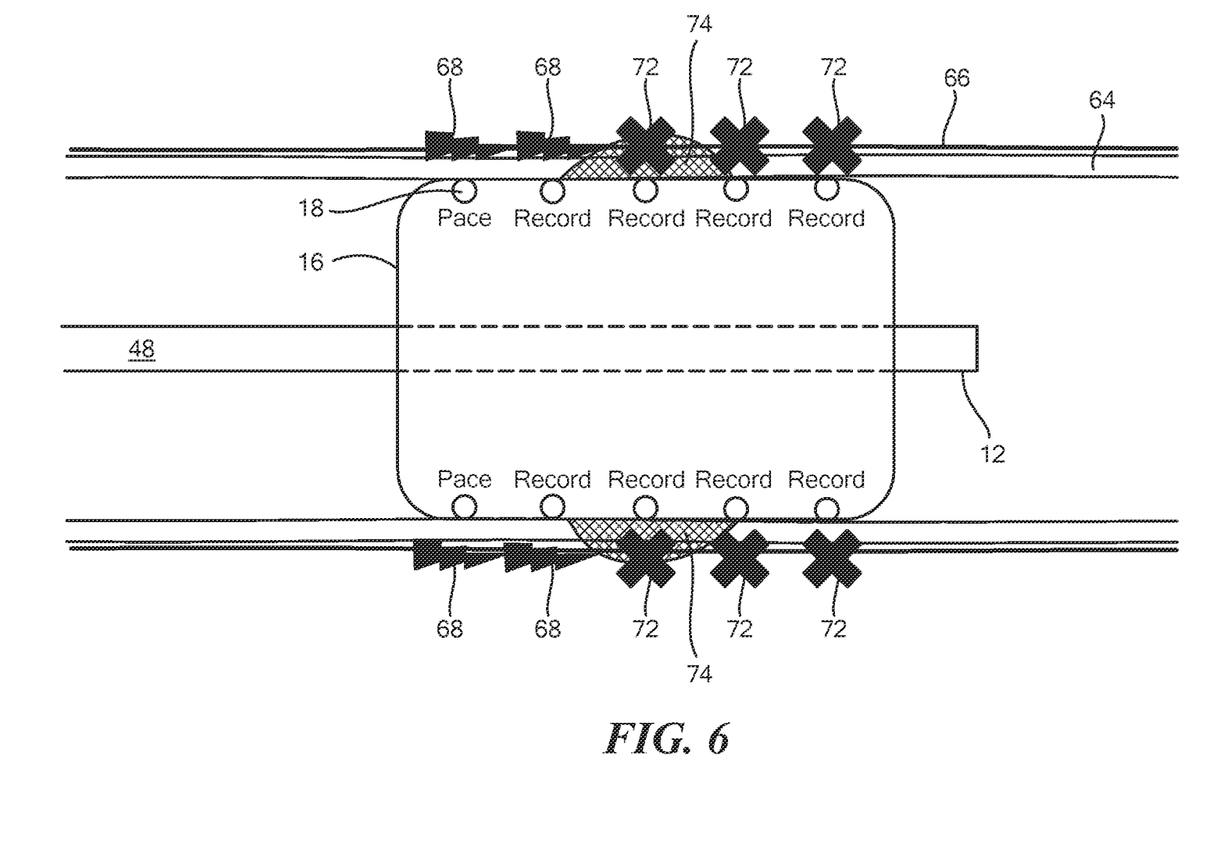
FIG. 6 is a side view of the simplified cryoablation device shown in FIG. 2 showing the resulting lesion and conduction block from a cryoablation procedure.

Referring now to FIG. 6, an example of Step 108, the locations marked with an "X" indicate that the electrical signals 68 are not measured at the particular electrode 18 indicating a conduction block 72 (diminished nerve function). Further, it is possible to stimulate bronchial nerves 66 with a series of electrical pulses of varying length and amplitude when using electrodes 18 in direct contact with tissue throughout the ablation process to monitor the reduction of conduction before a total loss of conduction. More specifically, the response of the bronchial nerves 66 will be a series of resulting pulses from electrodes 18 that will have reduced intensity depending on the degree of cooling until the conduction of pulses measured from the stimulated bronchial nerves 66 result in minimal measurement due to a conduction block 72 (reduction in nerve function). Data such as time to effect can be derived from such measurements taken during the ablation cycle and can be used to predict success (e.g., length of reversible nerve conduction loss).

Figure 7:
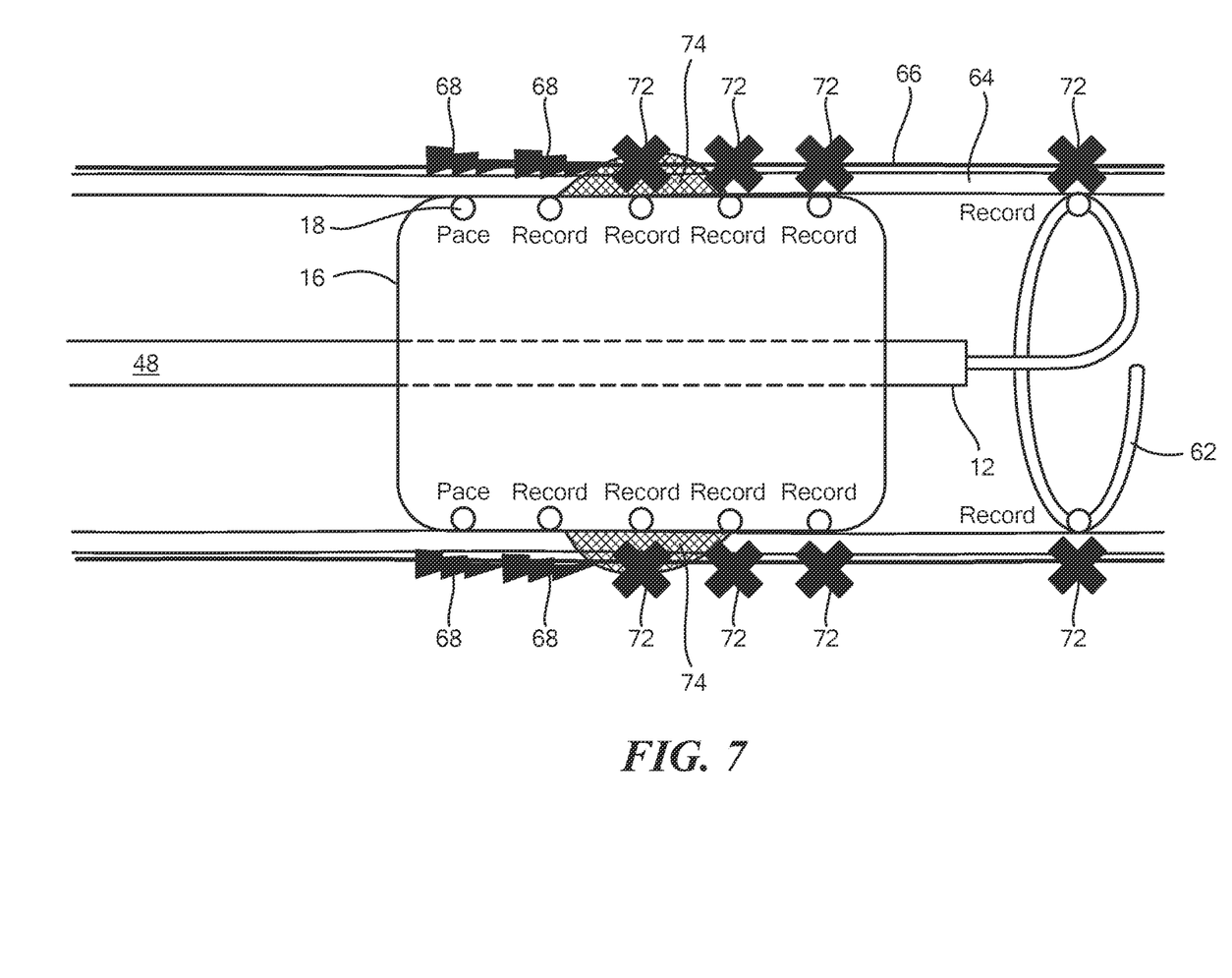
FIG. 7 is a side view of the simplified cryoablation device shown in FIG. 2 with a mapping catheter positioned distal to the cryoablation device and measuring a conduction block distal to the cryoablation device.

Once the bronchial nerve conduction block has been determined, the at least one bronchial nerve 66 is restimulated by the electrodes 18 at the conduction block 72 site (Step 110). In another configuration, the medical device 12 may include a circular mapping catheter 62. The restimulation of the bronchial nerve 66 can be performed with a medical device 12 with the mapping catheter 62. For example, as shown in FIG. 7, a circular mapping catheter 62, such as the Achieve™ manufactured by Medtronic, Inc. may be advanced through the shaft 32 to a position distal to the distal end of the balloon 16. In such a configuration, the medical device 12 with mapping catheter 62 may map the conduction block 72 to a location distal of the balloon 16 to confirm the conduction block 72 by sending and measuring electrical signals 68 via electrodes 18 at the conduction block 72 site. The use of a circular mapping device can lengthen the distance between the pacing and recording electrodes and can lead to better differentiation between the pacing signal and resultant nerve conduction signal.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible considering the above teachings without departing from the scope and spirit of the invention, which is limited only by the following claims.

What is claimed is:

1. A method of performing bronchial denervation of a bronchus having bronchial nerves along a portion thereof, comprising:
    providing a cryoablation device having a plurality of electrodes capable of delivering electrical energy and measuring impedance, each electrode of the plurality of electrodes positioned along a length of the bronchus;
    stimulating at least one bronchial nerve with electrical energy from at least a portion of the plurality of electrodes of the cryoablation device;
    recording electrical signals with each electrode of the plurality of electrodes from the stimulated at least one bronchial nerve to provide a first value representative of nerve function;
    applying cryogenic treatment energy using the cryoablation device to form ice having a thickness to encapsulate at least one bronchial nerve to cause a reduction in nerve function in the at least one bronchial nerve;
    restimulating the at least one bronchial nerve with electrical energy from at least a portion of the plurality of electrodes of the cryoablation device;
    recording electrical signals with each electrode of the plurality of electrodes from the restimulated at least one bronchial nerve to provide a second value representative of diminished nerve function; and
    comparing the first value and the second value to provide an assessment of the reduction in nerve function at a plurality of locations along the length of the bronchus.

2. The method of claim 1, further including repeating the following after comparing the first value to the second value if the second value is more than 50% of the first value:
    applying cryogenic treatment energy using the cryoablation device to form ice having a thickness to encapsulate at least one bronchial nerve to cause a reduction in nerve function in the at least one bronchial nerve;
    restimulating the at least one bronchial nerve with electrical energy from at least a portion of the plurality of electrodes of the cryoablation device;
    recording electrical signals from the restimulated at least one bronchial nerve to provide a third value representative of diminished nerve function; and
    comparing the first value and the third value to provide an updated assessment of the nerve function.

3. The method of claim 1, wherein the cryoablation device includes a balloon catheter having a plurality of electrodes disposed on an exterior surface of the balloon catheter.

4. The method of claim 3, wherein the cryoablation device includes an elongated flexible shaft extending from a distal end of the balloon, and wherein the elongate flexible shaft includes at least a portion of the plurality of electrodes.

5. The method of claim 1, further including introducing the cryoablation device within a bronchus prior to stimulating the at least one bronchial nerve.

6. The method of claim 1, further including measuring an impedance using at least a portion of the plurality of electrodes proximate the bronchial nerve.

7. The method of claim 6, further including correlating the measured impedance to ice thickness.

8. The method of claim 3, wherein the cryoablation device further includes a mapping catheter that extends distally from the balloon catheter to record electrical signals distal to the balloon catheter.

9. The method of claim 1, wherein the ice thickness is at least 3 mm.

10. The method of claim 1, wherein the electrical energy is non-ablative energy.

11. The method of claim 1, wherein the reduction in nerve function is permanent.

12. A method of performing bronchial denervation, comprising:
    advancing a catheter within a target bronchus, the catheter having a proximal portion and a distal portion having a balloon, the balloon including a plurality of electrodes circumferentially disposed about the balloon, each electrode of the plurality of electrodes positioned along a length of the target bronchus;

stimulating at least one bronchial nerve within the target bronchus with electrical energy from at least a portion of the plurality of electrodes;

recording electrical signals with each electrode of the plurality of electrodes from the stimulated at least one bronchial nerve along the length of the target bronchus;

delivering cryogenic treatment energy between the balloon and the target bronchus to form ice having a thickness to encapsulate at least one bronchial nerve in the target bronchus to reduce function in the at least one bronchial nerve;

restimulating the at least one bronchial nerve within the target bronchus with electrical energy from at least a portion of the plurality of electrodes; and determining that the function of the at least one bronchial nerve has been reduced by at least 50% at a location along the length of the target bronchus corresponding to an electrode of the plurality of electrodes.

13. The method of claim 12, wherein the reduction of nerve function by at least 50% indicates a conduction block, and wherein the conduction block is circumferential.

14. The method of claim 12, wherein the catheter includes an elongated flexible shaft extending from a distal end of the balloon, and wherein the elongate flexible shaft includes at least a portion of the plurality of electrodes.

15. The method of claim 12, wherein the ice thickness is at least 3 mm.

16. The method of claim 12, further including measuring an impedance proximate the at least one bronchial nerve with the plurality of electrodes.

17. The method of claim 16, further including correlating the measured impedance to ice thickness.

18. The method of claim 12, wherein the electrical energy is non-ablative energy.

19. The method of claim 12, wherein the reduction in nerve function is permanent.

20. A method of performing bronchial denervation, comprising:

providing a cryoablation device having a plurality of electrodes capable of delivering electrical energy and measuring impedance, the cryoablation device including a balloon catheter, and the balloon catheter having the plurality of electrodes disposed on an exterior surface, each electrode of the plurality of electrodes positioned along a length of a bronchus;

stimulating at least one bronchial nerve with electrical energy from at least a portion of the plurality of electrodes of the cryoablation device;

recording electrical signals with each electrode of the plurality of electrodes from the stimulated at least one bronchial nerve to provide a first value representative of nerve function;

applying cryogenic treatment energy using the cryoablation device to form ice having a thickness to encapsulate at least one bronchial nerve to cause a reduction in nerve function in the at least one bronchial nerve;

measuring an impedance with at least a portion of the plurality of electrodes proximate the bronchial nerve, and correlating the measured impedance to ice thickness in the target bronchus;

restimulating the at least one bronchial nerve with electrical energy from at least a portion of the plurality of electrodes of the cryoablation device;

recording electrical signals with each electrode of the plurality of electrodes from the restimulated at least one bronchial nerve to provide a second value representative of diminished nerve function;

comparing the first value and the second value to provide an assessment of the reduction in nerve function at a plurality of locations along the length of the bronchus;

applying cryogenic treatment energy using the cryoablation to form ice having a thickness to encapsulate at least one bronchial nerve to cause a reduction in nerve function in the at least one bronchial nerve;

measuring an impedance with at least a portion of the plurality of electrodes proximate the bronchial nerve, and correlating the measured impedance to ice thickness in the target bronchus;

restimulating the at least one bronchial nerve with electrical energy from at least a portion of the plurality of electrodes of the cryoablation device;

recording electrical signals with each electrode of the plurality of electrodes from the restimulated at least one bronchial nerve to provide a third value representative of diminished nerve function; and comparing the first value and the third value to provide an updated assessment of the nerve function at the plurality of locations along the length of the bronchus.

* * * * *